United States Patent
Wakefield et al.

(10) Patent No.: US 6,637,432 B2
(45) Date of Patent: Oct. 28, 2003

(54) INHALATION ACTUATED DEVICE

(75) Inventors: Keith Wakefield, Clayton, NC (US); Perry A. Genova, Chapel Hill, NC (US)

(73) Assignee: IEP Pharmaceutical Devices Inc., Raleigh, NC (US)

( * ) Notice: Subject to any disclaimer, the term of this patent is extended or adjusted under 35 U.S.C. 154(b) by 149 days.

(21) Appl. No.: 10/029,791

(22) Filed: Oct. 23, 2001

(65) Prior Publication Data

US 2002/0056449 A1 May 16, 2002

Related U.S. Application Data

(63) Continuation-in-part of application No. 09/567,352, filed on May 9, 2000, now Pat. No. 6,328,035.

(51) Int. Cl.[7] .............................................. A61M 15/08
(52) U.S. Cl. ......................... 128/203.23; 128/200.14; 128/200.23; 128/200.22; 128/203.12; 128/203.15
(58) Field of Search ..................... 128/200.14, 200.23, 128/200.22, 203.12, 203.23, 203.15

(56) References Cited

U.S. PATENT DOCUMENTS

| | | | | |
|---|---|---|---|---|
| 3,636,949 A | * | 1/1972 | Kropp | 128/200.23 |
| 3,789,843 A | * | 2/1974 | Armstrong et al. | 128/200.23 |
| 3,814,297 A | * | 6/1974 | Warren | 222/402.13 |
| 4,648,393 A | * | 3/1987 | Landis et al. | 128/200.23 |
| 5,027,808 A | * | 7/1991 | Rich et al. | 128/203.23 |
| 5,031,610 A | * | 7/1991 | Armstrong et al. | 128/200.23 |
| 5,060,643 A | * | 10/1991 | Rich et al. | 128/200.23 |
| 5,069,204 A | | 12/1991 | Smith et al. | |
| 5,119,806 A | * | 6/1992 | Palson et al. | 128/200.14 |
| 5,217,004 A | * | 6/1993 | Blasnik et al. | 128/200.23 |
| 6,328,035 B1 | * | 12/2001 | Wakefield et al. | 128/203.23 |

FOREIGN PATENT DOCUMENTS

| | | |
|---|---|---|
| GB | 2263873 A | * 11/1993 |
| WO | WO 82/01133 A1 | * 4/1982 |
| WO | WO 01/85245 A1 | 11/2001 |

* cited by examiner

*Primary Examiner*—Weilun Lo
*Assistant Examiner*—Darwin P. Erezo
(74) *Attorney, Agent, or Firm*—Frommer Lawrence & Haug, LLP; Ronald R. Santucci (57) ABSTRACT

A device for dispensing medication in an aerosol form from an MDI which is activated by a source of compressed air which is pressurized by a compression piston in associate with a cocking lever which also acts as a mouthpiece cover wherein the device automatically discharges the medication upon inhalation on the mouthpiece. The device also has a detachable component for alternative use as a press and breathe type inhaler.

18 Claims, 7 Drawing Sheets

INHALATION ACTUATED DEVICE

RELATED APPLICATION

This application is a continuation-in-part of U.S. patent application Ser. No. 09/567,352, filed May 9, 2000, now U.S. Pat. No. 6,328,035, the disclosure of which is hereby incorporated by reference.

BACKGROUND OF THE INVENTION

1. Field of the Invention

The present invention is directed to an inhalation actuated pulmonary drug delivery device used in the delivery of fluid dispensations from a drug containing canister, the delivery device providing a metered dose of drug or other therapeutic agent when the patient inhales from the device or when the patient compresses a canister section of the device.

2. Brief Description of Related Art

There are a variety of inhalation devices which release aerosol medication, either in a continuous spray or in a predetermined amount of medication, commonly referred to as a metered dose. The spray is applied directly into the patient's mouth, nasal area or respiratory airways. Typically, these devices are actuated by the pressure applied by the user's fingers, button action, or other related manual techniques. While there are devices which are activated by the inhalation of the users, some of which are very satisfactory, as with all things, variations or improvements are desirable.

Metered dose aerosol canisters of the medicine to be inhaled into the mouth, nasal areas or respiratory airways are manufactured by a variety of pharmaceutical companies. Therapeutic agents commonly delivered by the inhalation route include bronchodilators (B2 agonists and anticholinergics), corticosteroids, and anti-allergics. Inhalation may also be a viable route for anti-infective, vaccinating, systemically acting and diagnostic agents, as well as anti-leukotrienes, and-proteases and the like. Metered dose aerosols are much the same as non-metered aerosol except that when the valve is depressed, a continuous spray is not discharged. Instead, a predetermined measured volume is discharged as a spray, releasing a fixed amount of medication.

Metered dose inhalers are available in several types. Most frequently, metered dose inhalers comprise a chamber into which a pressure resistant container (canister) is placed. The container is typically filled under super-atmospheric pressures with a product such as a drug dissolved in a liquefied propellant, or micronized particles suspended in a liquefied propellant. The container is fitted with a metering valve. The valve is movable from an outer (charging) position to an inner (discharging) position. A spring bias holds the valve in the charged position until forced to the discharge position. Actuation of the metering valve allows a metered portion of the canister content to be released, whereby the pressure of the liquefied propellant carries the dissolved or micronized drug particles out of the container and to the patient. A valve actuator also functions to direct the aerosol as a spray into the patient's oropharynx. Surfactants are usually dissolved in the aerosol formulation and can serve the dual functions of lubricating the valve and reducing aggregation of micronized particles. Examples of such metered dose inhalers are disclosed in U.S. Pat. Nos. 5,514,647 entitled "Metered Dose Inhaler"; and 5,622,163 entitled "Counter for Fluid Dispensers"; and U.S. patent application Ser. No. 09/241,010 filed Feb. 1, 1999 entitled "Metered Dose Inhaler Agitator" (commonly assigned), the disclosures of which are incorporated herein by reference.

Representative of pharmaceutical formulations for use in metered dose inhalers are those described in U.S. Pat. No. 5,190,029. The metered dose inhalers for administering such pharmaceutical formulations are also well known as seen for example in the descriptions given in U.S. Pat. Nos. 3,361,306; 3,565,070; and 4,955,371 which are incorporated herein by reference.

A wide variety of fluid dispensers are known and commercially available to dispense metered proportions of a contained fluid from containers. For example, U.S. Pat. No. 3,749,290 describes a trigger actuated dispensing pump assembled with a fluid container. Upon actuation, a measured proportion of the contained fluid is dispensed from the containers.

"Pumping" type inhalers are known in the art. The device may be manually pumped (such as described in U.S. Pat. No. 5,284,132) or a pumping like cycle may be utilized. The medication may also be repeatedly released from a pressurized disposable canister to create repeated sprays or inhalations as needed.

Proper use of these manually actuated devices requires that the spray be activated at the beginning of the inspiratory cycle, so that the medication is carried into the lungs rather than being deposited in the mouth or throat. If this actuation is not correctly coordinated with the inspiratory phase, the metered dose may be deported differently with each actuation acrd potentially compromise the therapeutics and safety of the product.

There are numerous factors leading to poor coordination of actuation of the spray and the inspiration cycle. Included in those factors are the inherent limitations of the users (if any), such as impaired physical abilities associated with geriatric patients or the as-yet-undeveloped skills of children, or their inability of either group to comprehend the correct way to use the device. Recognizing the need for correct and accurately delivered doses in the asthmatics, COPD patients and, as with other patients with other respiratory illnesses, a reliable breath activated device would improve the quality of life for these afflicted people. Examples of breath-activated devices include U.S. Pat. No. 5,069,204 entitled "Inhaler" and U.S. patent application Ser. No. 09/567,352 entitled "An Inhalation Actuated Device", the disclosures of which are herein incorporated by reference.

SUMMARY OF INVENTION

It is therefore an object of the invention to provide an inhaler that is economical to manufacture, extremely easy to use, and delivers a metered dose of medicine, precise from dose to dose, in response to breath actuation and more particularly, in response to inspiration.

It is therefore a still further object of the present invention to provide an inhaler that is breath-actuated with an option of removing an included dispenser/mouthpiece assembly that is capable of press and breathe dispensing of a medicament.

To attain the objects described above, the present invention is directed to a pneumatically actuated, metered dose dispenser for an aerosol medication. The device has a housing defining a body portion into which the medicine-containing a canister is retained, and a mouthpiece for insertion into a patient's mouth. A mechanical lever with attached mouthpiece cover operates a compressor pump and after the device is pumped with a charge of compressed gas, maintained in a second chamber, a transfer valve is tripped by the vacuum formed when the user inhales from the device. This causes the compressed gas to enter a second chamber where the drug containing canister is maintained. This effects a depression of the canister valve stem, releasing the drug in an aerosol form. The release of the drug occurs at the same time as inhalation, insuring the delivery of a metered dose of medicine to the target location. In other words, the medicine is not mistargeted to the throat and upper mouth. The device of the present invention is relatively simple to operate, even by young children (6 to 12 years of age), and older patients as well, since inhalation initiates the dispensing of the drug.

An additional embodiment of the present invention is the ability to remove a dispenser/mouthpiece assembly attached within the housing of the device. Upon removal, the assembly can be used as a press and breathe type dispenser. This is advantageous as a backup if the breath-actuation feature of the device fails. In common use, the dispenser/mouthpiece assembly could be removed to replace expended dispensers.

BRIEF DESCRIPTION OF THE DRAWINGS

Embodiments of the present invention will be described with reference to the accompanying drawings in which.

DETAILED DESCRIPTION OF THE PREFERRED EMBODIMENTS

Figure 1:
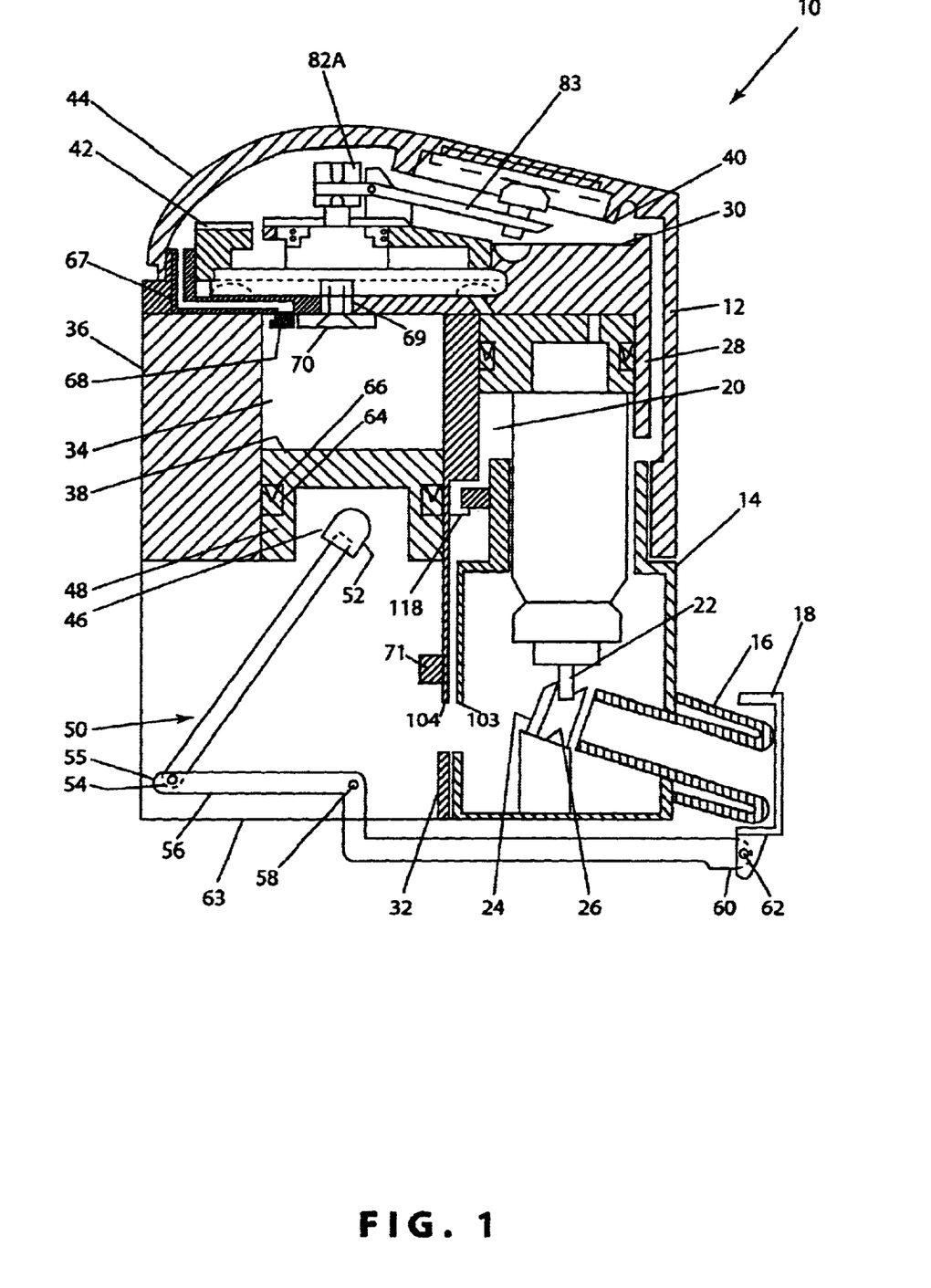
FIG. 1 is a cross-sectional view of the present invention showing the device in the at-rest position.

Turning now more particularly to the drawings, in FIG. 1 there is provided an inhalation actuated device 10, which comprises a housing 12 with a mouthpiece/canister assembly 14. Inhalation actuated device 10, depicted in FIG. 1, includes a detachable mouthpiece/canister assembly 14; however, the mouthpiece 16 and associated actuation components may be manufactured as part of device 10.

When the mouthpiece/canister assembly is operated, the canister stem 22 is impinged against surface 26, in response to displacement of the canister during a pressure actuation. The medicine is discharged from the canister stem as an aerosol. The nozzle 24 directs the spray outward through the mouthpiece 16.

In device 10, the first chamber 20 is defined by an outer wall 28, an upper surface 30 and a partitioning wall 32. A second chamber 34 is formed on the other side of partitioning wall 32, defined by the partitioning wall 32, upper surface 30, and outer wall 36. A movable piston 38 provides the lower surface of the second chamber 34. The volume of the second chamber is variable with respect to the location of the piston 38 within the chamber (shown in an at-rest position in FIG. 1). In operation, the piston is used to compress an initial volume of gas into a smaller one, thereby increasing the pressure of the gas. The energy stored in the compressed gas is used to effect the discharge of the medicine from the canister, as will be discussed.

There is a third chamber 40 in device 10, defined by the outer wall 28, upper surface 30, transfer valve cover 42, and airway cover 44. The third chamber 40 is a replenishable reservoir used to provide air to the second chamber 34 when resetting the movable piston 38, as will also be discussed.

The upper portion of the piston 38 is attached to lower piston support 46 forming compression piston assembly 48. Connecting link 50 is affixed to the compression piston assembly at first end 52. The second end 54 of the connecting link 50 is affixed to a first end 55 of the cocking lever 56. The cocking lever 56 is pivotally mounted about axial attachment rod 58, which fixedly attaches the cocking lever 56 to the housing. The second end 60 of the cocking lever 56 is affixed to the mouthpiece cover 18 at connecting pivot 62.

In operation, the cocking lever 56 pivots between an at-rest position and a charging position. When the inhalation device 10 is in an at-rest position, the cocking lever 56 rests in proximity to the underside 63 of the device and mouthpiece cover 18 protects mouthpiece 16.

Piston 38 is dimensioned to fit snugly against the inner walls of the second chamber 34, so that when the piston is moved into a cocked position, the fluid (gas, i.e. air) within the second chamber is compressed. The piston is provided with U-cup seals 64 which are situated within openings 66 in the piston 38, to prevent blowby leakage of compressed fluid around the sides of piston. In the-place of the piston seals, a rolling diaphragm seal, or a bellows-type system can also be used.

The upper surface 30 in the second chamber 34 also has a passage 67 in which an elastomeric umbrella check valve 68 is fitted. When the cocking lever 56 is moved towards the body of the device the connecting link 50 pulls the compression piston 38 downward. This action draws ambient air from the mouthpiece 16 or apertures 103 and 104 the third chamber 40 through passage 67, past the umbrella check valve 68 and into the second chamber 34.

The upper surface 30 in the second chamber 34 also has an aperture 69 into which a high pressure orifice 70 is fitted. As shown; in FIG. 2, when the cocking lever 56 is moved away from the mouthpiece 16 and toward the body of the device, the connecting link 50 pushes the compression piston 38 upwards. Cocking lever 56 and connecting link 50 are configured to toggle, so as to maintain the compression piston 38 near its upwardmost position prior to triggering. A toggle stop 71 is secured to partitioning wall 32, preventing over-action of the cocking lever 56.

The upward motion of the compression piston 38 pushes compressed fluid past the high pressure orifice 70 and against elastomeric diaphragm 72. The elastomeric diaphragm 72 is clamped at its periphery between the transfer valve cover 42 and the upper surface 30 of the housing to form an air tight seal. As shown, elastomeric diaphragm 72 borders space 73 and is provided as part of a fluid pathway 74. When the pathway 74 is open, the pathway 74 and second chamber 34 are in fluid communication with each other. Also provided is a transfer port 76, which is an orifice that is in fluid communication with chamber 20a, a sub-chamber of chamber 20. Chamber 20a is positioned between surface 30 and actuation piston 78 and is formed by the movement thereof. When the pathway 74 is open, the pathway 74 and chamber 20a are also in fluid communication with each other, and the compressed fluid can flow from the second chamber 34 to the chamber 20a, expanding the size of chamber 20a (more clearly shown in FIG. 3).

The actuation piston 78 is provided with U-cup seals 80. Prior to triggering, piston 78 is positioned at the upper end of chamber 20a. The lower portion of piston 78 abuts against canister 81.

There is little, if any, open volume in the space between the lower part of the upper surface 30 and the actuation piston 78. The actuation piston 78 fits snugly against the housing wall 12 and the partition wall 32, in order to form a seal that prevents leakage of the compressed fluid when it is released from the second chamber. Note that the actuation piston (and for that matter the compression piston) may take on a variety of forms including rolling diaphragms, bellows, etc. or other means suitable for purpose.

Above the diaphragm 72 there is a seat 82 that passes through the transfer valve cover 42 and presses against the diaphragm 72, providing a counterforce against the compressed air in the second chamber 34, insuring that the diaphragm is sealed.

At its top 82A, seat 82 engages an end of lever 83 which assists in triggering the diaphragm 72. The opposite end of lever 83 engages a compound diaphragm 86. The opposite side of diaphragm 86 is open to ambient air by way of aperture 88. Lever 83 is allowed to pivot about pivot point 84.

Biasing spring 98 serves to maintain diaphragm 72 in a sealed state prior to triggering and after the fluid has been compressed in chamber 34.

Figure 2:
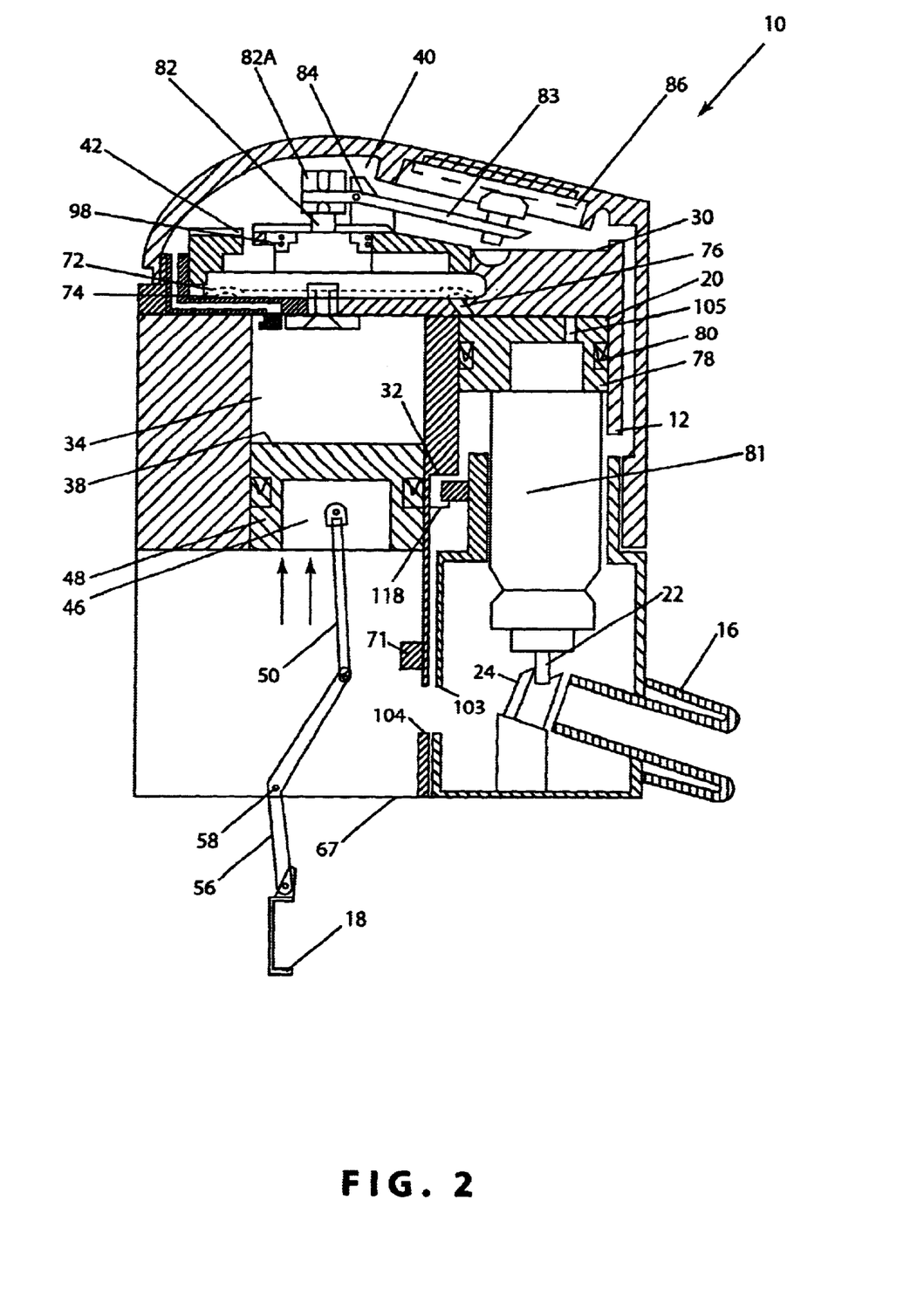
FIG. 2 is a cross-sectional view of the present invention showing the device in the cocking position.

The preferred embodiment described above is operated in the following manner. After the mouthpiece/canister assembly 14 has been loaded into the first chamber 20, the user flips the mouthpiece cover 18 away from its protecting position on the mouthpiece 16, such that the mouthpiece cover 18 is aligned with the cocking lever 56. The user then moves the cocking lever 56 toward the device and outward from the housing, as shown in FIG. 2. When the cocking lever is moved in this fashion, the connecting link 50 pushes the compression piston 38 upward. By forcing the compression piston 38 upward, volume in the chamber is reduced and the fluid in the chamber 34 is compressed.

Figure 3:
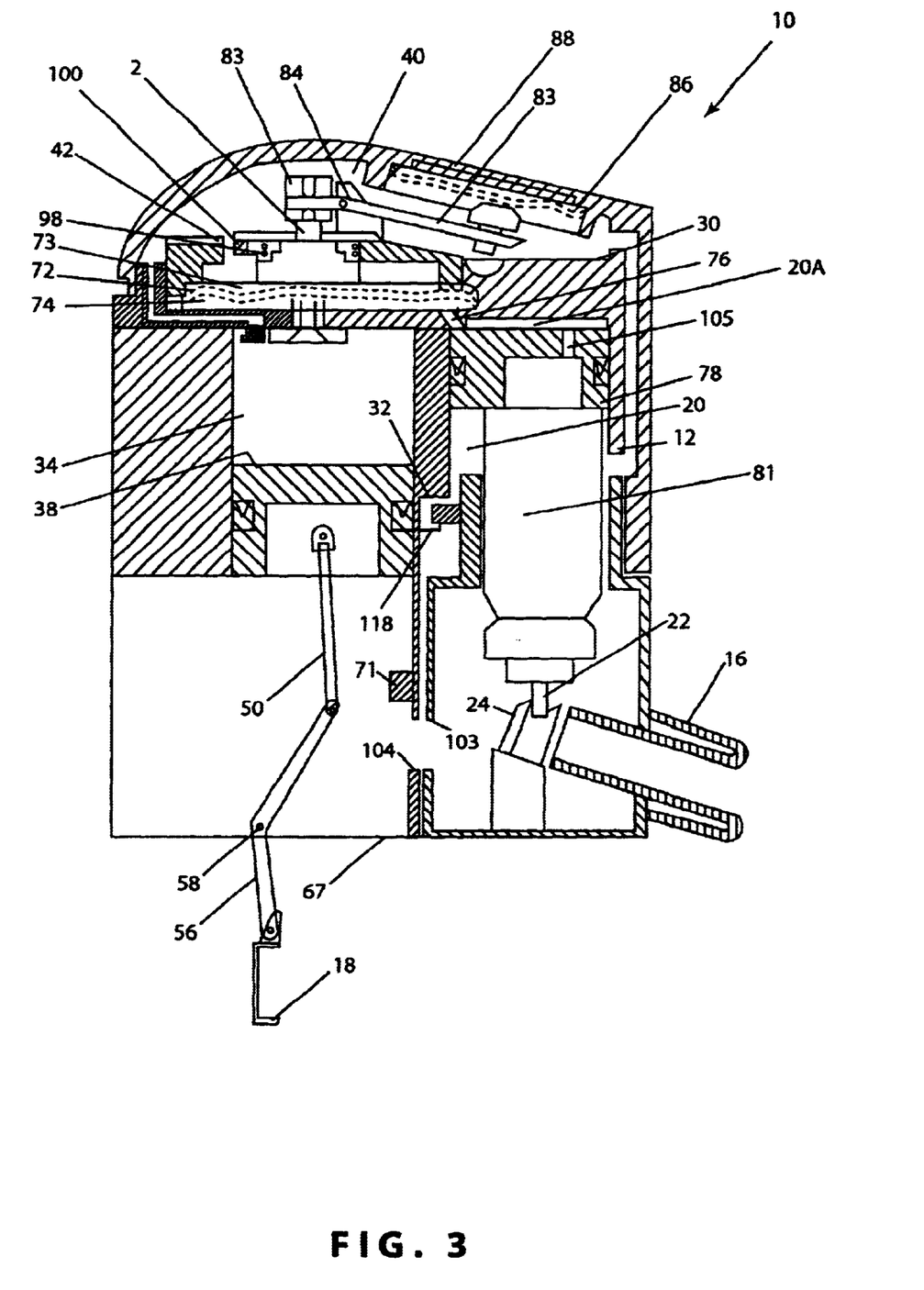
FIG. 3 is a cross-sectional view of the present invention showing the device in the fired position.

As shown in FIG. 3, when the user inhales through the mouthpiece 16, a vacuum is created inside the device (specifically, in the first and third chambers 20 and 40 and in the upper space 73 above fluid pathway 74 through vent orifice 100). The produced vacuum rapidly creates a differential pressure across the diaphragm 72 and compound diaphragm 86. For diaphragm 72, a threshold value is instantly exceeded at which point the biasing spring 98 can no longer keep the diaphragm in the sealed position. As part of this, the vacuum created causes diaphragm 86 to be sucked in to a certain degree causing lever 83 to pivot about pivot point 84 placing an upward force on seat 82. This in conjunction with the pressure differential created across diaphragm 72 causes it to snap open. Once open, the compressed fluid exits the second chamber 34, traverses the fluid pathway 74, and enters the first chamber 20 through transfer port 76, applying pressure to the actuation piston 78 and expanding chamber 20a. The force acting on the actuation piston 78 overcomes the return spring (not shown) in the canister stem 22, moving the canister 81 and/or stem to cause the dispensation of the medicine as an aerosol. The medicine is dispensed through the nozzle 24 and mouthpiece 16.

Note that when the user inhales, ambient air is drawn through apertures 103 and 104 allowing the user to breathe in whilst creating the pressure differential or vacuum signal that triggers the device. Accordingly, these apertures 103, 104 may be so sized so as to regulate the pressure drop within the device upon inhalation of the user and thus control the point at which the device is triggered. In addition, orifices 103, 104 provide fresh air to chamber 34 via chamber 20, pathway 28, chamber 40, and pathway 67.

A bleed orifice 105 in the crown of the actuation piston 78 slowly bleeds off the compressed air contained between the upper surface 30 and the piston 78, permitting the canister return spring to push the piston back to its original position, without user intervention. This prevents canister leakage that can occur if the valve stem remains depressed for prolonged periods. Moreover, as the pressure equalizes throughout the interior of the device, the biasing spring 98 returns the diaphragm 72 to the sealed position and lever 83 repositions itself.

The dwell time and air bleeding function of bleed orifice 105 is implemented by using a porous (7 $\mu$m) membrane inserted into a bore of actuation piston 78 where the bleed orifice is located. Using a porous membrane minimizes the chance that the bleed orifice becomes blocked or obstructed by debris.

It should be evident to the skilled artisan that inhalation and discharge of the medicine from the container is very quick, on the order of about 200 milliseconds, which insures that the inhalation of the medicine commences at the beginning of the inhalation, insuring delivery of the drug to a greater degree of targeted surface area, which ordinarily is the lungs, than is usually possible.

Figure 4:
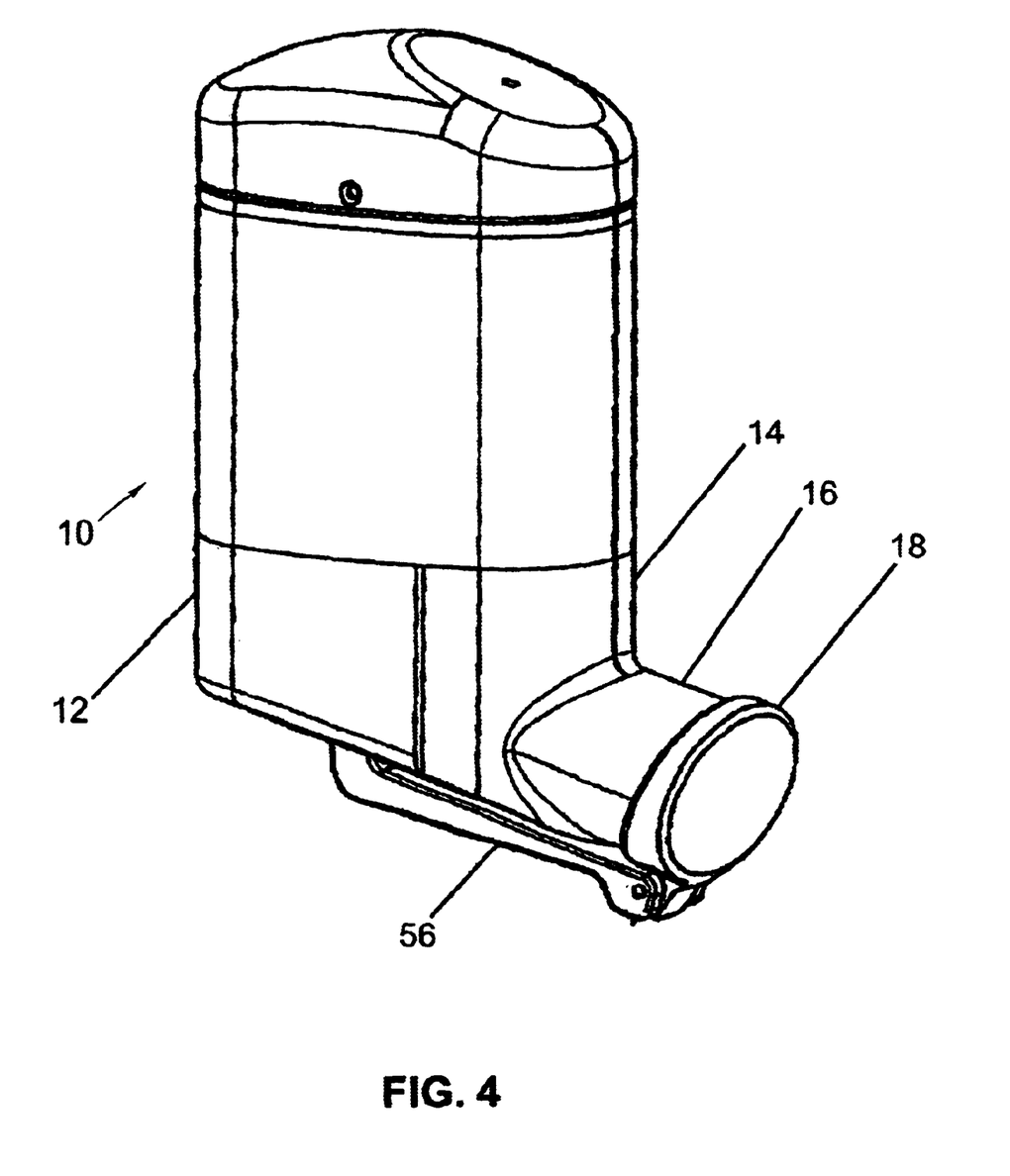
FIG. 4 is an exterior view of the present invention showing the device in the at-rest position.
Figure 5:
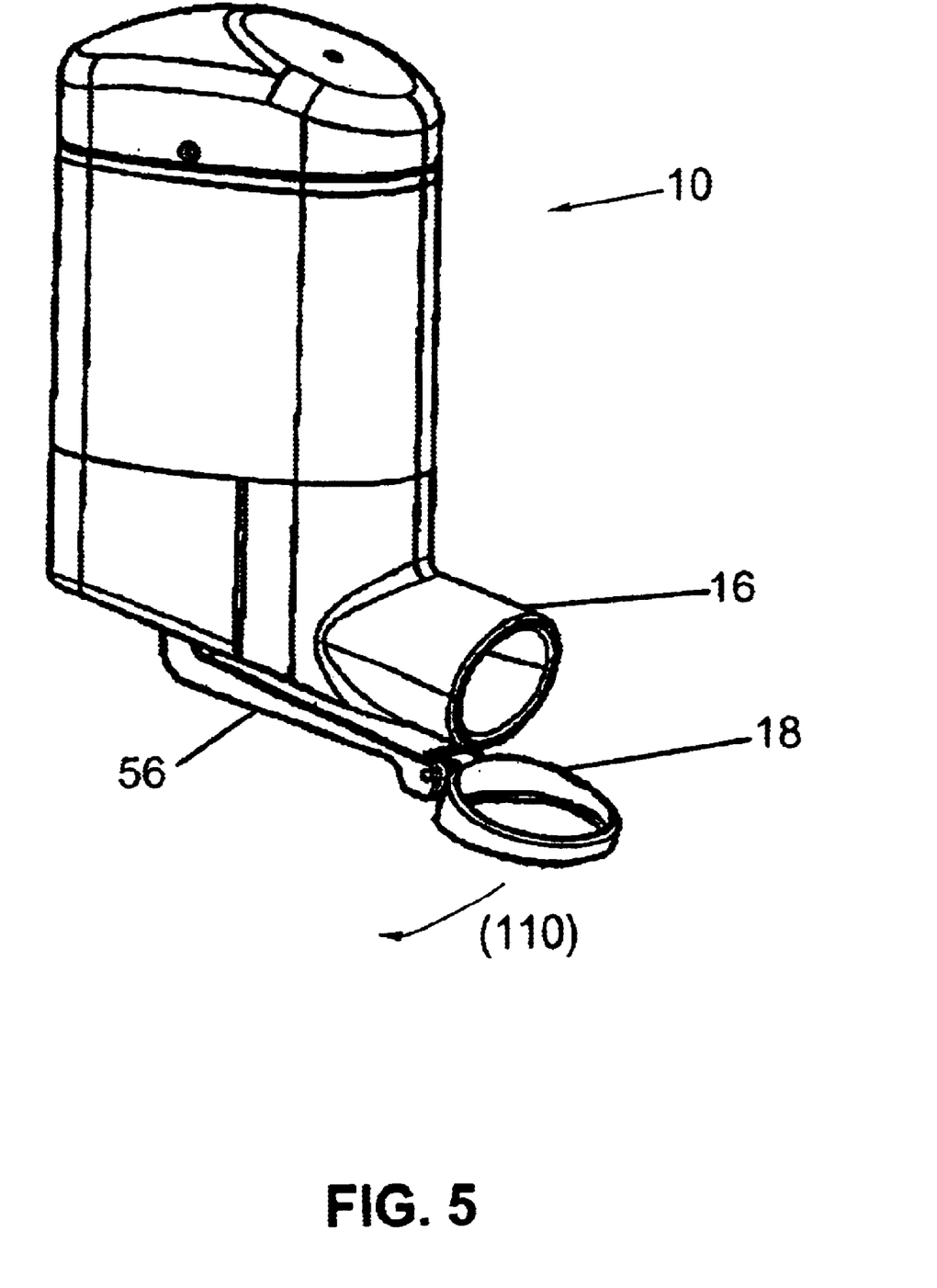
FIG. 5 is an exterior view of the present invention showing the mouthpiece cover removed.
Figure 6:
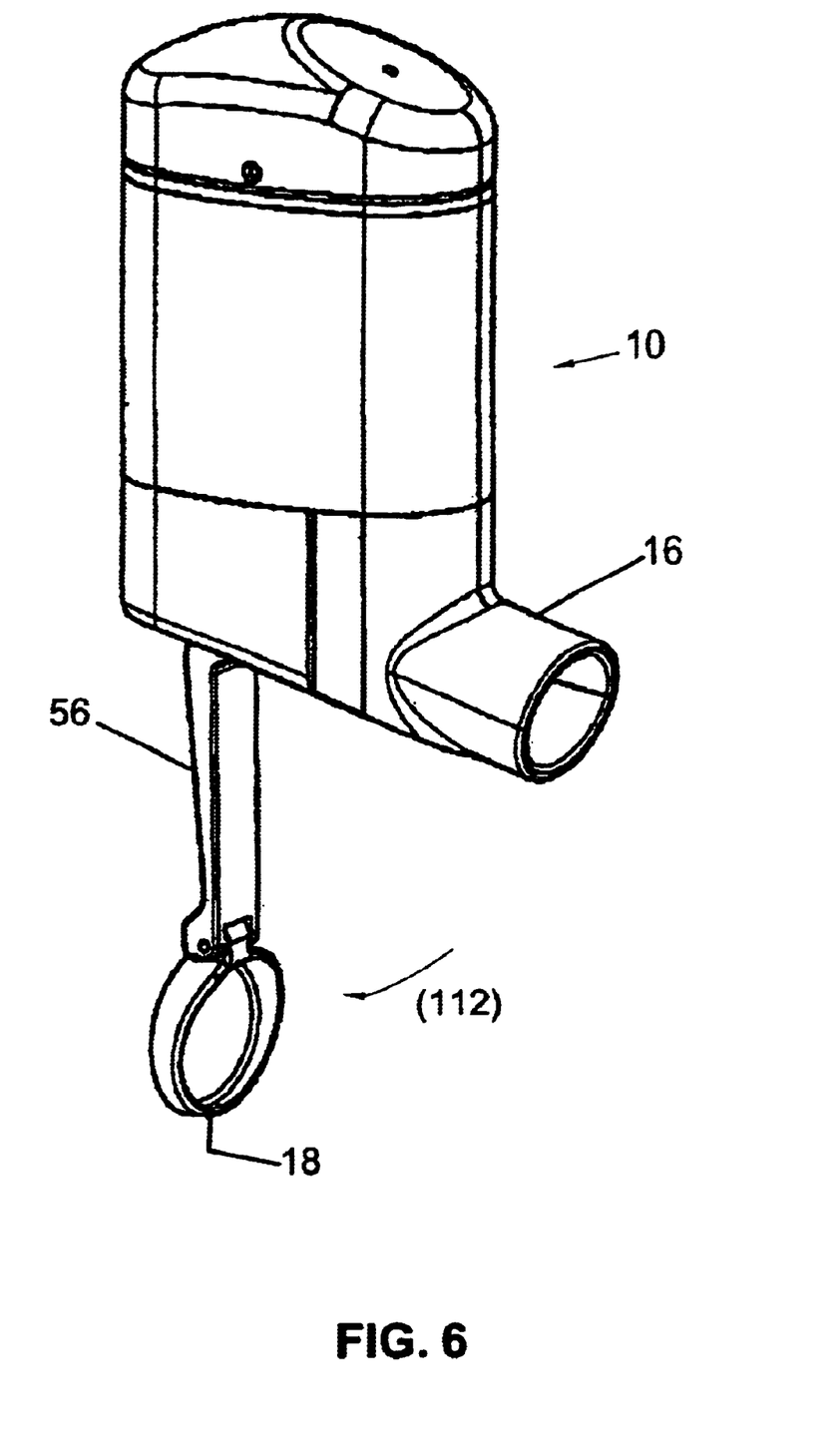
FIG. 6 is an exterior view showing the device in a cocked position.

Turning now more particularly to FIGS. 4–6 there is shown the exterior of the inhalation device 10 and its operation as it would appear to the user. FIG. 4 depicts the inhalation device 10 in an at-rest position. Mouthpiece 16 is protected by mouthpiece cover 18, with cocking lever 56 resting on the underside 63 of housing 12. The underside 67 of housing 12 may be notched to conformingly fit cocking lever 56. In FIG. 5, mouthpiece cover 18 is flipped in a downward direction 110 with mouthpiece 16 uncovered and cocking lever 56 ready for cocking.

In FIG. 6, cocking lever 56 is shown in its cocked position, after completion of movement in direction 112. Inhalation device 10 is now ready for use.

Figure 7:
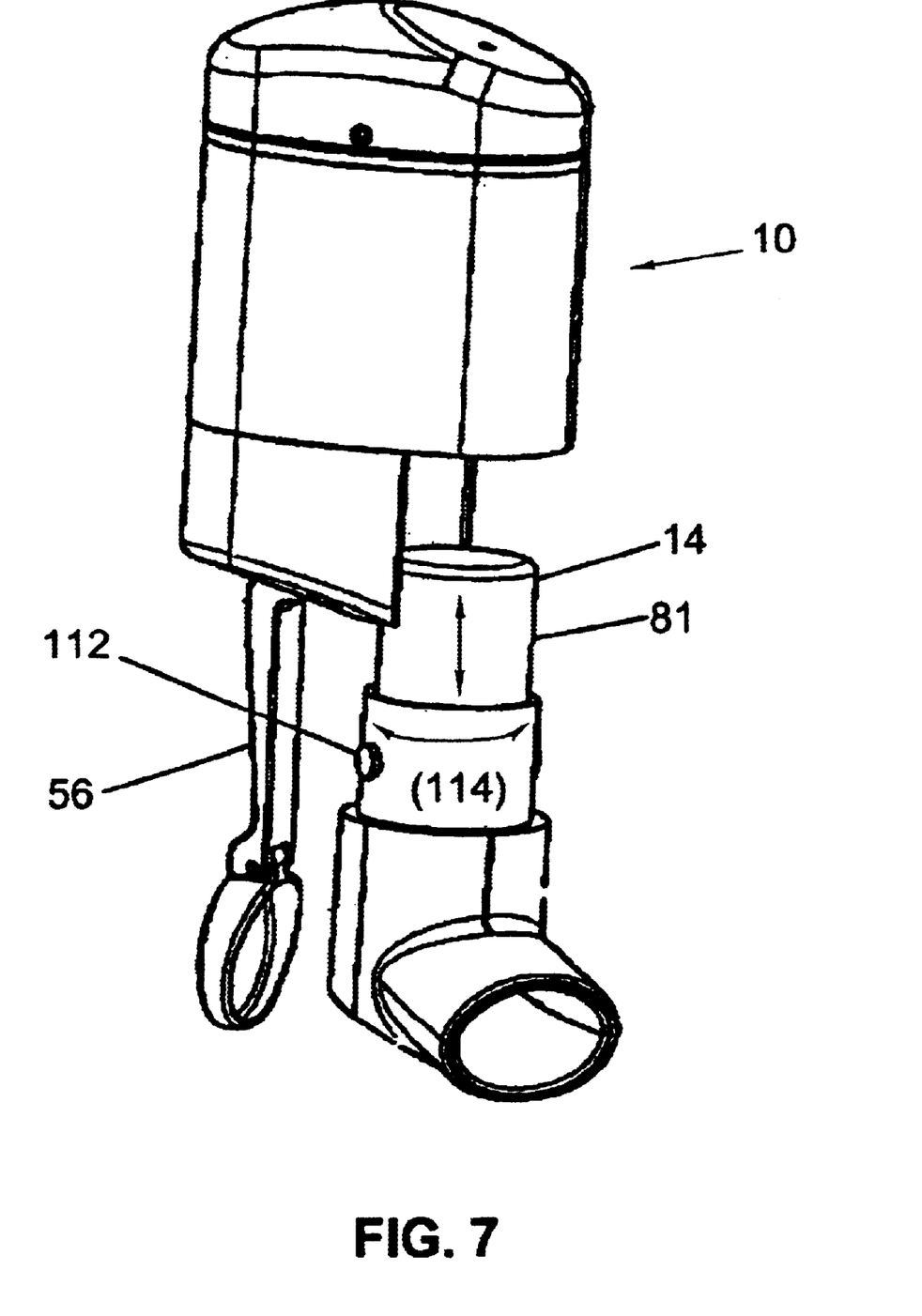
FIG. 7 is an exterior view of an alternative embodiment of the present invention showing detachment of a mouthpiece/canister assembly from the device.

In an alternative embodiment, mouthpiece/canister 14 is removable from inhalation device 10. As shown in its detached position in FIG. 7, mouthpiece/canister assembly 14 is detachable by means of a bayonet-type locking mechanism 112, which upon rotation 114 releases the mouthpiece/canister assembly 14. With cocking lever 56 in a firing position, mouthpiece/canister assembly 14 can be removed. With mouthpiece/canister assembly 14 removed, canister 81 can be easily changed or mouthpiece/canister assembly 14 can be used as a separate press and breathe type inhaler. When inserted, locking mechanism 112 rotates and interlocks with a slot 118 for securing the mouthpiece/canister assembly. In the at-rest position, cocking lever 56 and mouthpiece cover 18 provide additional securing of the mouthpiece/canister assembly within the inhalation device 10. Of course, other means of securing the mouthpiece/canister assembly 14 to the inhalation device 10 suitable for the purpose will be apparent to the skilled artisan.

The objects and advantages of the present invention are realized in accordance with the disclosure set forth above. Although preferred embodiments have been described in detail, the scope of the present invention should not be limited by this disclosure, but rather its scope should be determined by the appended claims.

What is claimed is:

1. A drug dispensing device actuated when a patient inhales from the device, comprised of
   (a) a first chamber for retaining a medication containing canister, the first chamber being in fluid communication with a mouthpiece through which a patient inhales a dose of a medication dispensed as an aerosol, an actuable means for acting on the canister causing dispensing of medication therefrom, said actuable means being in fluid communication with an openable and closeable first fluid pathway;
   (b) a second chamber including a compression piston hi to provide compression therein, the second chamber further including outlet means for providing fluid communication with the first fluid pathway;
   (c) a mouthpiece cover for protecting said mouthpiece wherein said mouthpiece cover is capable of rotating away from said mouthpiece;
   (d) a movable arm rotationally coupled at a first end to said mouthpiece cover and at a second end attached to the compression piston such that the compression piston is movable within said second chamber in response to movement of the movable arm in at least one direction causing compression of fluid therein;
   (e) sealing means for sealing the first said fluid pathway in a closed position; and
   (f) means for maintaining the sealing means in a closed position and for opening the sealing means when the differential pressure caused by the inhalation of the user exceeds a threshold value which causes said compressed fluid to act on said actuable means to displace said canister dispensing a close of medication to the user.

2. The device of claim 1 wherein the first chamber is provided with a receptacle positioned to impinge against a valve stem of the canister in response to the displacement of the canister or displacement of the valve stem.

3. The device of claim 1 wherein the first chamber is provided with an aperture sized to regulate a pressure drop within the device such that the differential pressure necessary to open the seal means may be adjusted.

4. The device of claim 1 wherein the second chamber is provided with an aperture for drawing a fluid into the second chamber.

5. The device of claim 4 wherein the aperture is provided with means to seal the second chamber when a fluid is compressed within the second chamber.

6. The device of claim 1 wherein the first fluid pathway is defined by a pathway between the actuable means and the second chamber.

7. The device of claim 1 wherein the sealing means comprises a first diaphragm located within the first fluid pathway.

8. The device of claim 6 wherein the sealing means comprises a first diaphragm located within the first fluid pathway.

9. The device of claim 1 wherein said means for maintaining the sealing means in a closed position comprises a biasing means which includes a compression-resisting spring biasing a first diaphragm in a closed position.

10. The device of claim 9 further comprising a pivotable lever assembly coupled to the first diaphragm.

11. The device of claim 10 wherein the pivotable lever assembly includes a second diaphragm engageable therewith.

12. The device of claim 11 wherein when the differential pressure across the second diaphragm exceeds a threshold value, the second diaphragm causes the pivotable lever assembly to cause an upward force on the first diaphragm to assist in causing said first diaphragm to open.

13. The device of claim 1 wherein said medication containing canister is operatively connected to a detachable dispenser, said detachable dispenser including said actuable means and said mouthpiece.

14. The device of claim 1 wherein the actuable means is provided with a bleed orifice means which controls a dwell time of the canister for delivering a dose of medication and allows the canister to return to a pre-activation position.

15. The device of claim 14 wherein said bleed orifice means is a porous membrane.

16. A drug dispensing device actuated when a patient inhales from the device, comprising:
   (a) a detachable dispenser, said dispenser including a mouthpiece through which a patient inhales a metered dose of medication dispensed as an aerosol;
   (b) a medication containing canister operatively connected to said detachable dispenser;
   (c) a first chamber for retaining said medication containing canister and said detachable dispenser, the first chamber being an actuator means for acting on the canister to dispense the medication therein,
   (d) a second chamber including a compression piston to provide compression therein, the second chamber further including means for allowing fluid communication with an operable and closeable first fluid pathway;
   (e) a movable arm attached at a first end to the compression piston such that the compression piston is movable within said second chamber in response to movement of the movable arm in at least one direction causing compression of fluid therein;
   (f) means for sealing the first fluid pathway in a closed position; and
   (g) means for maintaining the sealing means in a closed position and for opening the scaling means when the differential pressure thereacross exceeds a threshold value at which time compressed fluid passes through said fluid pathway to said first chamber causing said actuator means to displace said canister dispensing a dose of medication to the user.

17. The drug dispensing device of claim 16 wherein said detachable dispenser includes a bayonet-type interlocking mechanism.

18. The drug dispensing device of claim 17, further including a mouthpiece cover rotatably coupled to a second end of said movable arm, wherein said mouthpiece cover is capable of rotating away from said mouthpiece.

* * * * *